United States Patent
Rao et al.

(10) Patent No.: US 6,366,689 B1
(45) Date of Patent: Apr. 2, 2002

(54) 3D PROFILE ANALYSIS FOR SURFACE CONTOUR INSPECTION

(75) Inventors: Sreenivas Rao; Noor Ashedah Binti Jusoh; Wong Soon Wei; Tan Seow Hoon; Satish Kaveti, all of Singapore (SG)

(73) Assignee: ASTI, Inc. (SG)

( * ) Notice: Subject to any disclaimer, the term of this patent is extended or adjusted under 35 U.S.C. 154(b) by 0 days.

(21) Appl. No.: 09/418,056

(22) Filed: Oct. 14, 1999

(51) Int. Cl.[7] ................................................. G06K 9/00
(52) U.S. Cl. ....................................... 382/145; 382/154
(58) Field of Search ................................. 382/141–149, 382/152, 154, 150; 348/86, 87, 125, 126; 702/57, 58, 59, 155; 356/394; 250/559.45, 559.46, 226

(56) References Cited

U.S. PATENT DOCUMENTS 4,269,515 A * 5/1981 Altman ........................ 356/394
5,003,495 A * 3/1991 Thibadeau et al. .......... 382/145
5,946,645 A * 8/1999 Rioux et al. ................. 702/155
5,963,664 A * 10/1999 Kumar et al. ................ 382/154

* cited by examiner

Primary Examiner—Joseph Mancuso
Assistant Examiner—Vikkram Bali
(74) Attorney, Agent, or Firm—Christopher J. Rourk; Akin Gump Strauss Hauer & Feld, LLP (57) ABSTRACT

A system for inspecting a component is provided. The system includes an imaging system, such as a digital camera. A controller is connected to the digital camera. The controller receives the digital image data of a device that is generated by the camera. The controller processes the digital image data to generate control commands. A variable grid generation system is also connected to the controller. The variable grid generation system can receive commands from the controller, and can generate a grid in response to the commands that matches the component and that allows the component to be inspected.

8 Claims, 4 Drawing Sheets

3D PROFILE ANALYSIS FOR SURFACE CONTOUR INSPECTION

FIELD OF THE INVENTION

The present invention relates to inspection systems, such as those used to inspect surface mount type semiconductor devices, and more particularly to systems and methods for inspection of components that illuminate the components with a grid.

BACKGROUND OF THE INVENTION

Unintended damage and deformation of semiconductor devices and components is a well-known problem in the semiconductor industry. Inspection systems and methods have been developed to detect damage to semiconductor devices and components, but these inspection systems and methods are not able to detect all damaged systems and components before they are shipped to a customer. In addition, many of these inspection systems and methods require significant amounts of operator time.

One inspection system and method for detecting damage to semiconductor devices and components is to illuminate the semiconductor device or component with a grid, and to use the grid as an aid in the inspection of the device or component. Although such systems and methods utilizing illumination with a grid are useful, they are subject to certain drawbacks. One drawback is that the grid is generated using an etched template, and this template must be replaced for each different device or component that is inspected. Replacing the template requires operator intervention. Furthermore, the grid illumination must be centered on each device or component, which also requires operator intervention. Finally, each device or component must be aligned within a narrow tolerance to an inspection plane, or else the degree of tilt of the device or component can lead to a spurious indication that the device or component is damaged.

SUMMARY OF THE INVENTION

Therefore, a need exists for a system and method for inspecting devices or components by illuminating the devices or components that overcomes known systems and methods for inspecting devices or components.

In particular, a system and method for inspecting devices or components by illuminating the devices or components with a grid is required that does not require an operator to replace a template for each new device or component, does not require the operator to align the grid on each device or component, and does not require the device or component to lie in an inspection plane.

In accordance with the present invention, a system for inspecting a component is provided. The system includes an imaging system, such as a digital camera. A controller is connected to the digital camera. The controller receives digital image data of a device that is generated by the camera. The controller processes the digital image data to generate control commands. A variable grid generation system is also connected to the controller. The variable grid generation system can receive commands from the controller, and can generate a grid in response to the commands that matches the component and that allows the component to be inspected.

The present invention provides many important technical advantages. One exemplary important technical advantage of the present invention is that it generates a grid for illuminating a component but does not require an operator to replace a template for each new device or component. In this manner, a series of different components may be inspected without requiring an operator to change a template or mask for each different component.

Another important technical advantage of the present invention is that it allows a device to be analyzed without requiring the operator to align the grid on each device or component. The present invention aligns the grid on a device or component based upon an analysis of the image data of the device or component.

Other technical advances represented by the invention, as well as the objects thereof, will become apparent from the following description of a preferred embodiment of the invention when considered in conjunction with the accompanying drawings, and the novel features set forth in the appended claims.

DETAILED DESCRIPTION OF PREFERRED EMBODIMENTS

In the description which follows, like parts are marked throughout the specification and drawing with the same reference numerals, respectively. The drawing figures may not be to scale and certain components may be shown in generalized or schematic form and identified by commercial designations in the interest of clarity and conciseness.

Figure 1:
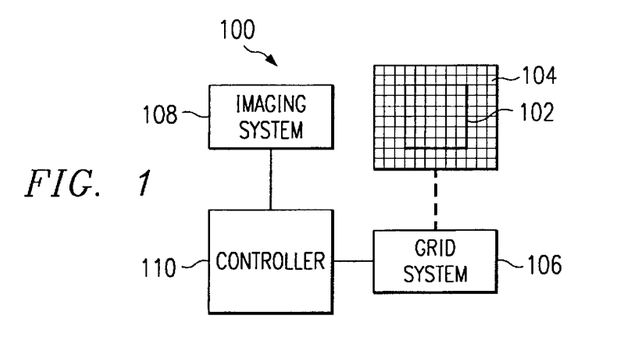
FIG. 1 is a diagram of a system for inspecting components in accordance with an exemplary embodiment of the present invention.

FIG. 1 is a diagram of a system 100 for inspecting components in accordance with an exemplary embodiment of the present invention. System 100 may be used to illuminate a component with a grid in order to aid in the automatic inspection of the component.

System 100 includes component 102 and grid 104. Component 102 may be a semiconducting device in a package with leads, or other suitable components. Grid 104 is projected onto component 102 so as to illuminate component 102. Grid 104 may be generated by a suitable lighting system, such as a laser lighting system, a light source that is directed through a template, or other suitable lighting systems.

Grid 104 is aligned with component 102 such that features of component 102 are illuminated by grid 104. For example, component 102 may include a plurality of leads, such as leads that are used to electrically connect component 102 with other systems, components, or devices. Grid 104 may be aligned with the leads, such that one grid line runs the length of each lead, and another grid line intersects perpendicularly with each of the first grid lines. In this manner, the location of each lead may be determined. In addition to alignment with leads, grid 104 may be aligned to other or additional features of component 102.

Grid system 106 may be implemented in hardware or a suitable combination of hardware and software, and is used to generate grid 104. For example, grid system 106 may include one or more laser devices that are operable to generate a laser beam having controllable or known beam characteristics, in conjunction with mirrors or other devices or systems that cause the laser beam to move so as to trace out a grid pattern. For example, the laser beam generated by grid system 106 may be a red or green 15 milliwatt visible laser, with a beam width of approximately 1–150 microns in diameter. Multiple color lasers may be used so as to allow the component or device to be inspected through packing tape or other similar materials that may be reflective or that otherwise cause light to be scattered or deflected. Other suitable lasers may be used. Likewise, grid system 106 may use a non-coherent light source that is used to illuminate component 102 through a template with a controllable grid aperture, such as a liquid crystal diode template. The template of grid system 106 may be controlled such that grid 104 on component 102 aligns with the features of component 102.

Imaging system 108 is a digital imaging system that is operable to generate a digital image of component 102 as illuminated by grid 104. Imaging system 108 may be implemented in hardware or a suitable combination of hardware and software. In one exemplary embodiment, imaging system 108 is a charge coupled device photo imaging system. Imaging system 108 is operable to generate plurality of picture element or pixel data points with a brightness that corresponds to the perceived brightness of component 102 as illuminated by grid 104. For example, imaging system 108 may be a 1024×1024 pixel or any size imaging array that is operable to store a brightness value matrix corresponding to an image, where the matrix is used to form a 1024×1024 pixel grid. Imaging system 108 typically obtains an image of the component or device over a period of time in which one or two grid lines are traced, and will refresh the image during the period of time that the next two grid lines are traced until a complete image is formed. This process is required because of the speed of the grid pattern generation and the length of time required for the imaging system 108 to generate an image.

Imaging system 108 and grid system 106 are coupled to controller 110. As used in this application, the term 'couple and its cognate terms such as "coupled" or couples" may be used to denote a physical connection (such as through a copper conductor or a data bus), a virtual connection (such as through randomly assigned memory locations of a memory device), a logical connection (such as through logical gate devices of a semiconducting component), a combination of such connections, or through other suitable connections or combinations of connections. For example, connections through intervening devices or components may be used where suitable.

Controller 110 may be implemented in hardware, software, or a suitable combination of hardware and software, and may be one or more software systems operating on a general purpose computing platform. As used in this application, a software system may be implemented as one or more related objects, one or more related subroutines, distributed code throughout compiled source code, or other suitable software structures that operate in a coordinated manner to process data so as to perform the described functions. Controller 110 is operable to receive image data from imaging system 108, and to generate grid control commands for grid system 106. Controller 110 may also be operable to receive imaging data of component 102 as illuminated by grid 104, and to determine whether grid 104 illuminates desired features of component 102. If grid 104 does not illuminate desired features of component 102, controller 110 can generate commands to cause grid system 106 to correct any error between the existing configuration of grid 104 and the desired configuration of grid 104.

Controller 110 is also operable to analyze the digital image data received from imaging system 108 of component 102 illuminated by grid 104, so as to analyze the condition of component 102. For example, controller 110 may determine whether leads of component 102 have a desired configuration, such as whether the leads have become bent or otherwise damaged.

Controller 110 is also operable to correct the image data for component 102 as illuminated by grid 104 to compensate for an angular displacement of component 102. For example, if component 102 is sitting in a plane that is at an angle as compared to the plane that is normal to imaging system 108, the illumination of component 102 by grid 104 may result in an uneven illumination. Such uneven illumination may produce misleading results if controller 110 is unable to determine whether component 102 is at an angle from the normal angle to imaging system 108. Controller 110 is operable to analyze image data from imaging system 108 to determine whether component 102 is at an angle from normal, and to compensate the image generated by imaging system 108 to compensate for such angle.

For example, controller 110 may determine from the grid data whether the digital image data of the device or component is indicative that the device or component is at an angle from the normal plane to the imaging system. The device or component may have bent leads that are oriented such that they normally appear straight as illuminated by the grid. If each such lead includes a discontinuity, such as a break in a grid line at a location where a bend occurs, then controller 110 can determine the angle from normal of the component based upon the number of leads having such discontinuities, and the angular location of the discontinuity relative to the other grid lines.

In another exemplary embodiment, the apparent separation between leads of a device or component that is in a plane that is angularly displaced from the normal viewing plane will appear to be unevenly distributed, due to perspective. Leads of a device that is tilted will appear to be closer together than leads of a device that is not tilted with respect to the viewing vantage point. If it is known that the leads are evenly spaced, then this known perspective effect may also be used to determine the angle from normal of the plane in which the device lies.

In operation, system 100 is used to inspect a component 102 to determine whether the component has been damaged or has otherwise become unsuitable for use. For example, component 102 may include a plurality of leads, of which one or more may become bent during handling. Grid 104 is generated by grid system 106, and is used to illuminate the leads or other features of component 102. Imaging system 108 creates a digital image of component 102 as illuminated by grid 104, and this digital image data is analyzed by controller 110 to determine whether any leads or other features of component 102 have become damaged. If component 102 is determined to be damaged, or other questionable circumstances are indicated, controller 110 generates a suitable signal indicating that further operator attention is required, such as to remove the component. Controller 110 may also generate control commands for a component handling system to remove the device or component without operator intervention.

Figure 2:
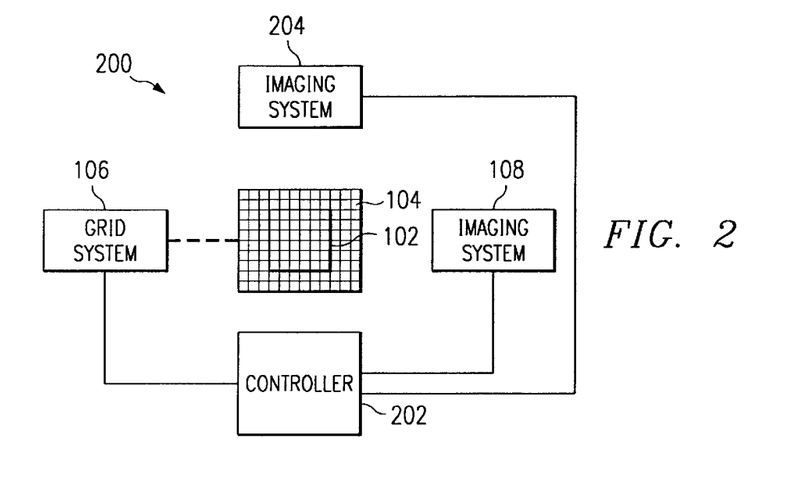
FIG. 2 is a diagram of an inspection system for inspecting a component, in accordance with an exemplary embodiment for the present invention.

FIG. 2 is a diagram of an inspection system 200 for inspecting a component, in accordance with an exemplary embodiment for the present invention. Inspection system 200 includes dual imaging systems 108 and 204 that can compensate for obscured portions of component 102, such as portions that are obscured by packing material, or to compensate for reflections and light scattering caused by packing material.

Inspection system 200 includes controller 202, grid system 106, imaging system 108, and imaging system 204. Imaging system 204 is similar to imaging system 108, but is oriented at a different angle to component 102. Grid 104 is used to illuminate component 102, and imaging system 108 and 204 are used to generate image data of component 102 as illuminated by grid 104. Controller 202 is operable to receive the imaging data from imaging system 108 and the imaging data from imaging system 204, and to analyze the two images to determine whether any features of component 102 are absent from one or the other of the image data generated by imaging system 108 and imaging system 204. In this manner, controller 202 may determine whether features that have been obscured to one or the other of imaging system 108 and imaging system 204 should be analyzed for damage, or other purposes.

For example, controller 202 may map component 102 based upon imaging data received from imaging system 108, and may also map component 102 based upon imaging data received from imaging system 204. Controller 202 may then compare the two maps on a pixel by pixel basis or other suitable basis. If it is determined that pixels of one map are not included on pixels of the other map, those pixels may be used to form a composite map. This composite map is then adjusted, such that the difference in angular perspective of imaging systems 108 and 204 are compensated for. The composite map is then used to analyze the component or device for defects or damage.

In operation, inspection system 200 is used to inspect components, such as component 102, and may be used in a transfer or storage configuration. For example, if component 102 has been placed in a pocket of a tape storage media or tray storage media, then a single imaging system such as imaging system 108 may not be able to obtain the full image data of component 102, as the walls of the storage media may obstruct parts of the device or component. Inspection system 200 uses dual imaging systems, such as imaging system 108 and imaging system 204, to obtain image data of component 102 as illuminated by grid 104 from more than one viewing angle. The dual image data sets may then be compared to verify whether a complete set of image data has been obtained, and to update the image data with supplemental image data. In this manner, controller 202 may analyze component 102 for damage regardless of the potential obstruction of component 102 by the storage media from imaging system 108 or imaging system 204.

Figure 3:
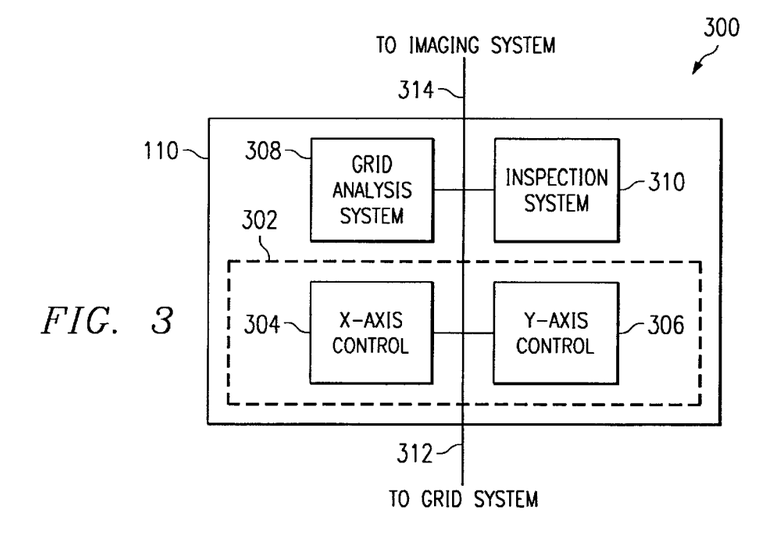
FIG. 3 is a diagram of a controller system in accordance with an exemplary embodiment of the present invention.

FIG. 3 is a diagram of a controller system 300 in accordance with an exemplary embodiment of the present invention. Controller system 300 may be used to process image data and to generate grid control data for use in an inspection system, such as inspection system 100 or inspection system 200.

Controller system 300 includes controller 110, which also includes grid control system 302, grid analysis system 308, and inspection system 310. Controller system 300 is coupled to an imaging system such as imaging system 108 or imaging system 204 by data bus 314, and is coupled to a grid system such as grid system 106 by a data bus 312. Controller system 300 receives image data from data bus 314, and generates transmit control data over data bus 312.

Grid control system 302 is operable to generate grid control commands based upon data received from grid analysis system 308 and inspection system 310. Grid control system 302 may be operable to generate control commands for individual axes, such as for controlling individual axis control devices for tracing a grid. In this exemplary configuration, grid control system 302 may include an X-axis control system 304 and a Y-axis control system 306. Grid control system 302 may alternatively generate grid pattern commands instead of x-axis and y-axis tracing commands, such as for a grid generator that does not require individual axis control commands for tracing the grid.

X-axis control system 304 and Y-axis control system 306 may be implemented in hardware, software or a suitable combination of hardware and software, and may be software systems operating on a general purpose computing platform. X-axis control system 304 and Y-axis control system 306 receive data from grid analysis system 308 and convert the data into control commands that may be used to generate the grid by tracing the grid. For example, grid analysis system 308 may generate a set of data points through which the grid should pass. These data points may be converted by X-axis control system 304 and Y-axis control system 306 into suitable commands for controlling the tracking or tracing of a laser beam. These data points may also be used to control the opaqueness of a material in a controllable mask or template, such as a liquid crystal diode template, or for other suitable systems.

For example, X-axis control system 304 may generate motion control commands for a galvanometer that is coupled to a mirror, such that the mirror moves in a controllable manner in response to control signals transmitted to the galvanometer. X-axis control system 304 may thus control the x axis coordinates of the laser beam by controlling the motion of the mirror attached to the galvanometer. Likewise, Y-axis control system 306 may control the motion of another galvanometer that is coupled to another mirror. X-axis control system 304 and Y-axis control system 306 are coordinated to generate commands to cause the laser beam to trace out a grid pattern and illuminate the component 102 with the grid, so that the grid may be used by grid analysis system 308 and inspection system 310 to inspect the component for possible damage.

Grid analysis system 308 may be implemented in hardware, software, or a suitable combination of hardware and software, and may be a software system operating on a general purpose computing platform. Grid analysis system 308 is operable to receive image data from imaging system 108 and to analyze the image data to determine features of component 102. For example, grid analysis system 308 may determine the angular difference between a reference plane and the plane in which component 102 lies. If component 102 is disposed in a packing media, such as a tape packing media or a tray packing media, it may be sitting at an angle from a normal plane angle to the imaging system 108. Grid analysis system 308 is operable to analyze the grid data to determine whether the component is lying at such an angle.

Grid analysis system 308 is also operable to determine the coordinates of grid 104 based upon preliminary imaging data for component 102, and may also determine whether grid 104 illuminates the desired features of component 102. For example, grid analysis system 308 may receive initial image data for component 102, and may then generate grid coordinates based upon the identification of features of component 102. If component 102 includes a plurality of leads based around the periphery of component 102, then grid analysis system 308 may analyze the image data to identify the lead coordinates, and may generate control commands for causing the grid system 106 to generate a grid 104 that will illuminate the leads. Other features of a component or device may also be illuminated. Grid analysis system 308 may also analyze the component illuminated by the grid, so as to verify that the grid is illuminating the desired features, to provide additional illumination of features that appear to be problematic, or for other suitable purposes.

Inspection system 310 receives data over data bus 314 from imaging system 108, and analyses the image data to determine whether the component 102 has been damaged or otherwise contained anomalies. For example, when grid 104 illuminates component 102, a straight lead may result in an illumination that presents a straight row of pixels. If the lead is bent, however, then the grid 104 illumination of that lead may be shorter, longer, or broken, as compared with the expected illumination pattern. Inspection system 310 is operable to compare the illumination of the features of component 102 with expected and allowable variations, and to generate an alarm or other operator signal that indicates that component 102 may be damaged or unacceptable. Inspection system 310 may also generate commands for a component removal system (not explicitly shown) that will cause the component removal system to remove the damaged component and replace it with another component, which may then be inspected.

Controller system 300, X-axis control system 304, Y-axis control system 306, grid analysis system 308, and inspection system 310 may be self-contained software systems, or may also or alternatively comprise distributed software functionality within one or more software systems. Likewise, functional components of controller system 300, X-axis control system 304, Y-axis control system 306, grid analysis system 308, and inspection system 310 may be objects, subroutines, or associated software systems residing on control, computing, or memory devices or systems of imaging system 108 and grid system 106.

In operation, controller system 300 is used to receive data over data bus 314 from an imaging system, to analyze the data so as to generate grid control commands, to generate control commands for a grid system 106, to receive image data of the component illuminated by the grid 104, to determine whether the grid 104 has suitable coordinates, to generate correction commands to realign grid 104 over the desired features of component 102, and to analyze component 102 as illuminated by grid 104 to determine whether component 102 has been damaged or is otherwise unacceptable or anomalous. Controller system 300 thus replaces many functions that are currently performed by an operator, such as the aligning of the component 102 so that it falls within an acceptable plane, selection of a grid template such that the grid generated falls on a the desired features of the component, and analysis of the illuminated component when the component is at an angle to a normal plane of observation.

Figure 4:
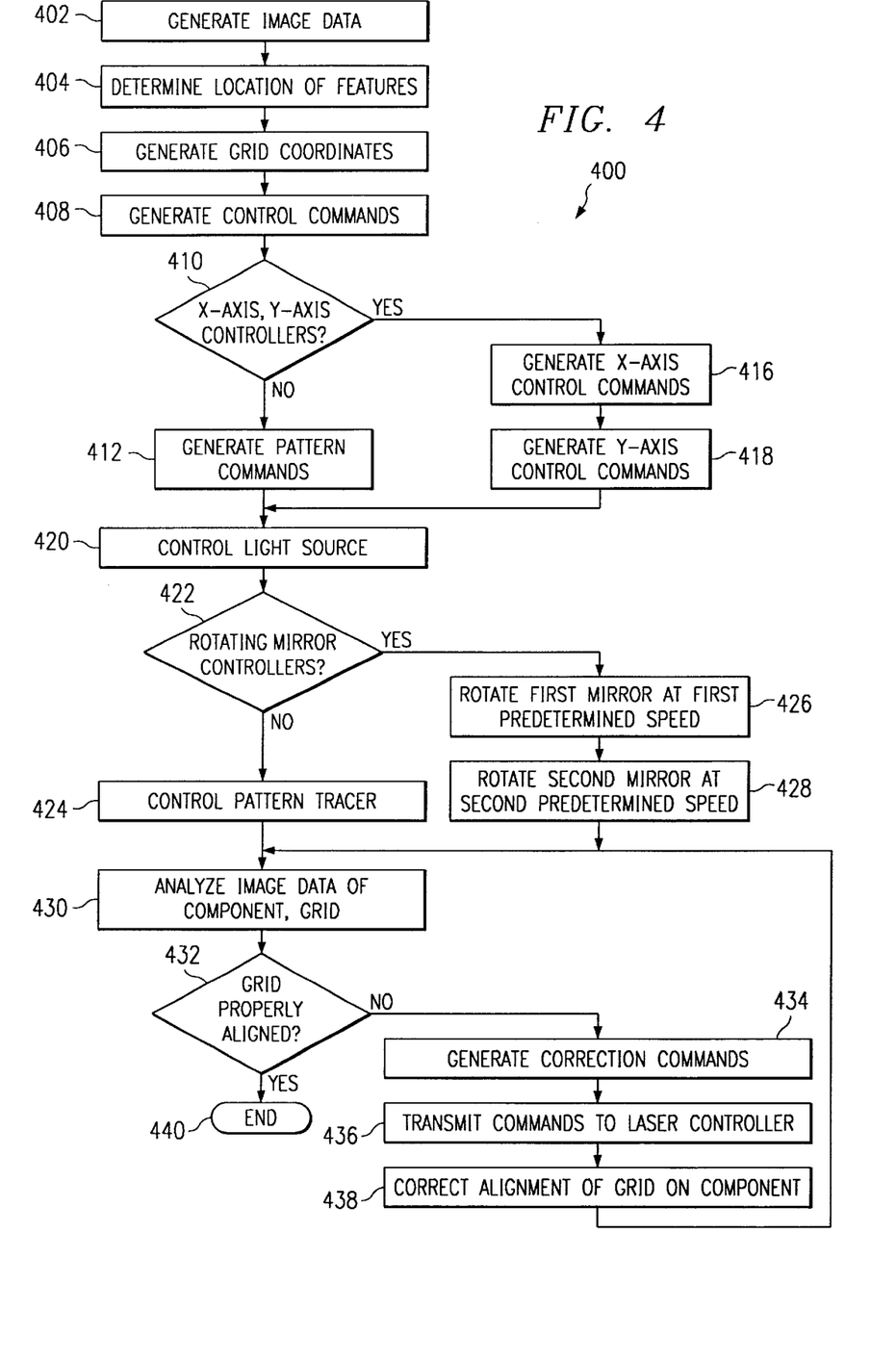
FIG. 4 is a flow chart of a method for generating a grid to illuminate a component in accordance with an exemplary embodiment of the present invention.

FIG. 4 is a flow chart of a method 400 for generating a grid to illuminate a component in accordance with an exemplary embodiment of the present invention. Method 400 may be used to generate a variable grid that does not require replacement of masks or templates when a new component is being inspected.

Method 400 begins at 402 where image data is generated while a component is being tested. The method then proceeds to 404 where the location of predetermined features is determined from the image data. For example, the predetermined features may include leads that surround the periphery of the component, such that the location of the leads may be determined by comparing the dimensions of pixel groups, pattern matching, or by using other suitable methods of data analysis. After the features are located, the method proceeds to 406 where coordinates are generated. For example, the grid coordinates may be determined by identifying all features and determining a set of coordinates that intersect with all of the features at one or more locations. The method then proceeds to 408.

After 408, control commands are generated to control the generation of the grid. For example, the control commands may be generated for a laser Illumination system that traces out a grid design to illuminate the component with a grid. Likewise, the control commands may be generated for a suitable variable masking or template system, such as a liquid crystal diode with controllable grid parameters. The method then proceeds to 410 where it is determined whether X-axis and Y-axis controllers are being used. If X-axis and Y-axis controllers are not being used, the method proceeds to 412 where pattern commands are generated, such as commands for forming a template on a programmable template system. Otherwise, the method proceeds to 416.

At 416, X-axis control commands are generated. For example, X-axis control command may include commands for causing a galvanometer to move in a manner that corresponds to X-axis deflections of the laser beam. Such control commands will be dependent upon the dimensions of the mirror used to deflect the laser beam, the spacing between the component and the laser beam and the mirror, and other important physical features of the inspection system. The method then proceeds to 418 where Y-axis control commands are generated. Y-axis control commands are generated in a similar manner to the X-axis control commands, and may require commands for controlling the movement of a galvanometer. After the X-axis and Y-axis control commands are generated at 416 and 418, the method proceeds to 420.

At 420, a light source is controlled to generate the grid pattern and to eliminate the component. For example, a light source may be illuminated through a template or mask to form a grid on the component if a controllable template or mask system is used. Otherwise, a laser beam or other suitable light source may be turned on, or multiple laser beams may be used, such as a red laser beam, a green laser beam, or other suitable combinations of laser beams. The method then proceeds to 422.

At 422, it is determined whether mirror controllers are being used to generate the template grid pattern. If it is determined at 422 that mirror controllers are not being used, the method proceeds to 424 where the pattern tracer is controlled. For example, the grid pattern may be made by tracing a pattern with the laser beam, by physically moving the laser apparatus, or by creating a pattern in a liquid crystal mask or template system. If it is determined at 422 that mirror controllers are used, the method proceeds to 426.

At 426, a first mirror is moved to control the X-axis movement of the laser beam or laser beams. For example, a galvanometer may be coupled to a mirror which is moved in a manner that is directly correlated with an X-axis deflection for the laser beam. The method then proceeds to 428 where a second mirror is moved to cause the Y-axis deflection of the laser beam. In this manner, a grid patter may be generated by X-axis and Y-axis deflection of the laser beam by the movement of mirrors. The method then proceeds to 430.

At 430, analysis of the image data of the component as illuminated by the grid is initiated. The image data is analyzed at 432 to determine whether the grid is properly aligned. If it is determined at 432 that the grid is not properly aligned, the method proceeds to 434 where correction commands are generated. For example, the difference between the actual and the desired location of the grid may be calculated, and movement commands for a galvanometer control for the X-axis or Y-axis controllers may be calculated. The method then proceeds to 436.

At 436, the commands are transmitted to the laser controllers. The method then proceeds to 438 where the alignment of the grid on the component is corrected, such as by altering the movement of the galvanometers. The method then returns to 430 to determine whether the illumination of the component by the grid is proper. If it is determined at 432 that the grid is properly aligned, the method proceeds to 440 and terminates.

In operation, method 400 is used to illuminate a component with a grid, and may be used to verify that the grid is properly aligned on the component. Method 400 is typically used prior to inspection of the component, to verify that a grid has been generated and is being used to illuminate the component in the manner required to allow the component to be inspected.

Figure 5:
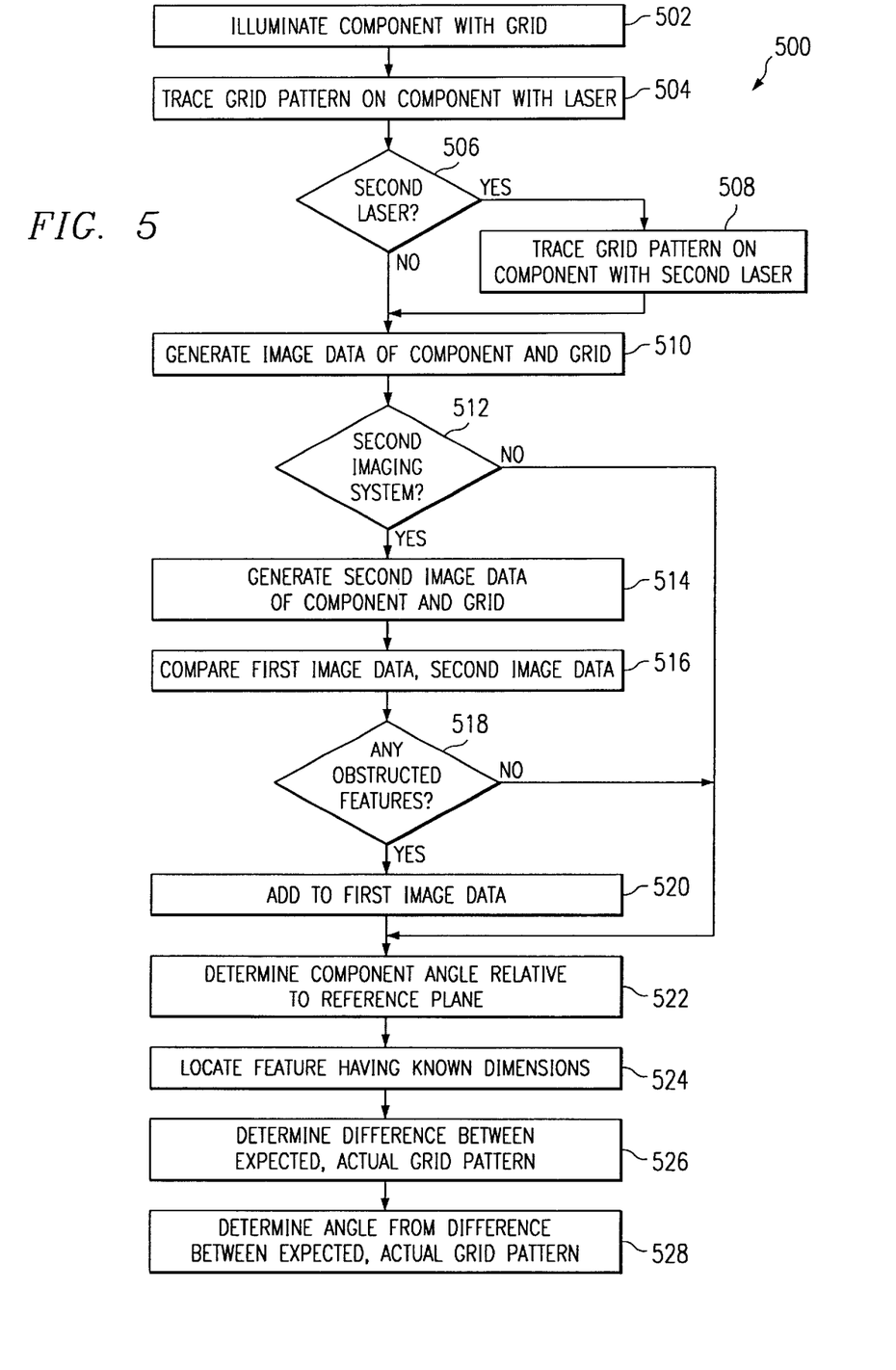
FIG. 5 is a flow chart of a method for inspecting a component in accordance with an exemplary embodiment of the present invention.

FIG. 5 is a flow chart of a method 500 for inspecting a component in accordance with an exemplary embodiment of the present invention. Method 500 may be used with a variable grid generation system to analyze a component that is sitting at an angle from a plane that is normal to an imaging device, and to determine whether additional obstructed features of the component exist.

Method 500 begins at 502 where a component is illuminated with a grid. For example, the grid coordinates may be determined by a suitable system or method, and grid control commands may be generated to cause the component to be illuminated with the grid. The method then proceeds to 504 where a grid pattern is traced on the component with a laser. For example, a laser may be deflected by mirrors such that the laser controllably generates a grid illuminating the features of the component. The method then proceeds to 506 where it is determined whether a second laser is being used. If the second laser is being used, such as a green laser in addition to a red laser, the method proceeds to 508 where a grid pattern is traced on the component using the second laser in addition to the first laser. The lasers may alternatively be traced simultaneously. Otherwise, the method proceeds directly to 510.

At 510, an image data set of the component illuminated by the grid is generated. For example, a charge coupled device or other suitable digital image generation system may be used to generate the image of the component illuminated by the grid. The method then proceeds to 512 where it is determined whether a second imaging system is being used. If the second imaging system, the method proceeds to 514 where a second image data set of the component, as illuminated by the grid, is generated. The method then proceeds to 516, where the first image data set and second image data set are compared to determine whether any features of the component have been obscured in the first image data set or the second image data set.

For example, the component may be disposed within a tape packing media such that portions of the component are obscured in either the first image data set or the second image data set. The method then proceeds to 518, where it is determined whether there are any obstructed features. If it is determined that obstructed features exist, the method proceeds to 520 where the image data for the obstructed features are combined to form a complete image data set. The method then proceeds to 522.

At 522, the determination of the component angle relative to a reference plane is initiated. For example, the component may be in a plane that is at an angle to a plane that is normal to the imaging system. The image data may be corrected before it may be analyzed to determine whether there is damage to the component. At 524, a feature having known dimensions is located, such as a component lead or the spacing between component leads. The method then proceeds to 526 where the difference between the actual and expected grid pattern is determined. For example, the features having known dimensions such as leads will generate an expected grid pattern if no damage has been caused to these features. If the features are damaged, the illumination by the grid will generate lines that are not existent, broken, or otherwise indicative of damage. Such features are excluded from the angular displacement analysis. The method then proceeds to 528 where the difference between the expected and actual image data is used to determine the angle from a normal plane of the plane in which the device or component lies. This angle is determined for each data point with respect to the angle at which the data point was taken when composite image data from two or more imaging systems is used.

In operation, method 500 is used to create an image data set for inspecting a device in order to determine whether the device has been damaged or contains other anomalies. Method 500 can use multiple light sources and multiple image sets, so as to compensate for inspecting components through a transparent barrier, such as packing tape. Method 500 also compensates for the angular orientation of the component relative to a normal plane. Thus, method 500 eliminates the need for operator intervention for component inspection for many conditions that currently require operator intervention.

Figure 6:
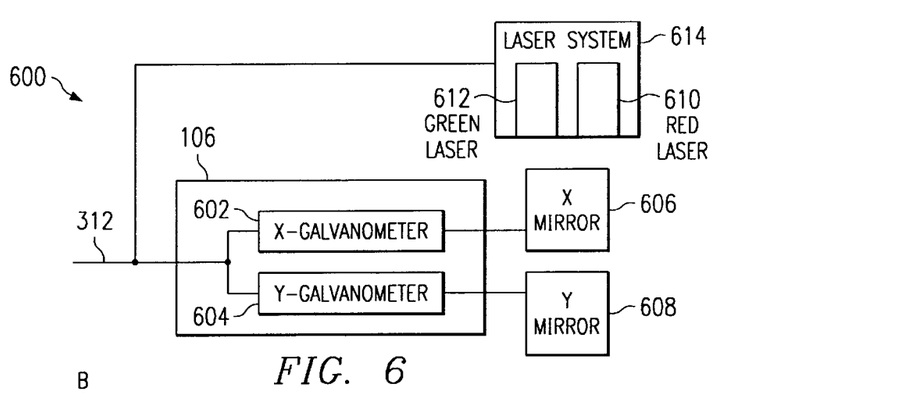
FIG. 6 is a diagram of a grid system in accordance with an exemplary embodiment of the present invention.

FIG. 6 is a diagram of a system 600 in accordance with an exemplary embodiment of the present invention. System 600 may be used to generate a variable grid on a component, such that it is not necessary to replace a fixed template for inspection of the component or to adjust the component so that it sits within a predetermined allowable angle from a reference plane.

System 600 includes grid system 106 which is coupled to data bus 312. Grid system 106 receives control commands from data bus 312. Grid system 106 includes X-galvanometer 602 and Y-galvanometer 604. X-galvanometer 602 is a suitable galvanometric device that can cause X-mirror 606 to move in a direction so as to cause a laser beam that is directed at X-mirror 606 to be deflected along the X-axis. Y-galvanometer 604 is coupled to Y-mirror 608, and is operable to deflect Y-mirror 608 so as to cause the laser beam to be deflected along the Y-axis by a controllable amount. X-galvanometer 602 and Y-galvanometer 604 operate in a coordinated manner to create a grid pattern by deflecting a laser beam to trace out a predetermined grid having predetermined coordinates that are based upon the image data of the component being analyzed.

Laser system 614 is coupled to data bus 312 and includes red laser 610 and green laser 612. Red laser 610 and green laser 612 may be 15 milliwatt visible lasers having a beam width of approximately 150 microns in diameter. Red laser 610 and green laser 612 are operable to be controllably activated so as to form a grid on a component for subsequent analysis of the component.

In operation, grid system 106 is used to form a grid on a component 102. Red laser 610 and green laser 612 of system 600 trace a grid pattern on a component. This grid pattern is used to analyze features of the component to determine if they are damaged or otherwise outside of specified tolerances.

Figure 7A:
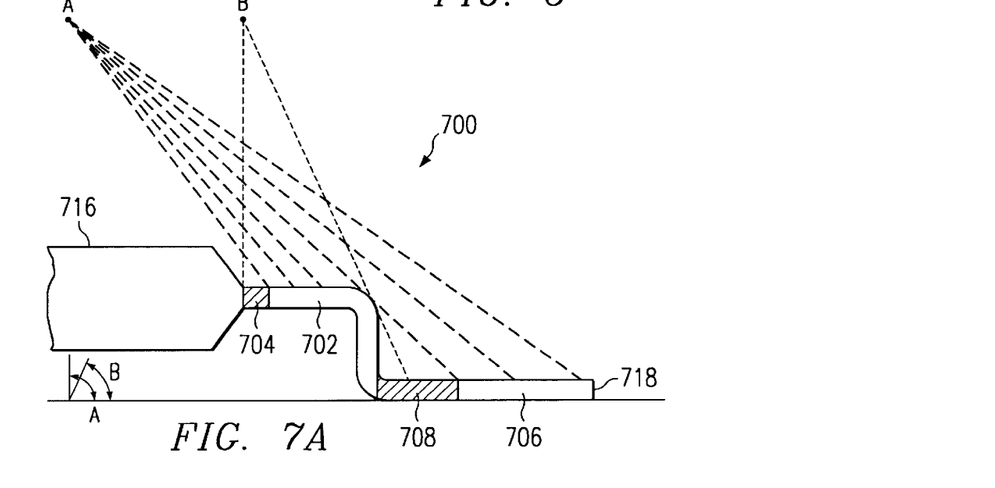
FIGS. 7A and 7B are diagrams showing illumination of a device or component in accordance with exemplary embodiments of the present invention.
Figure 7B:
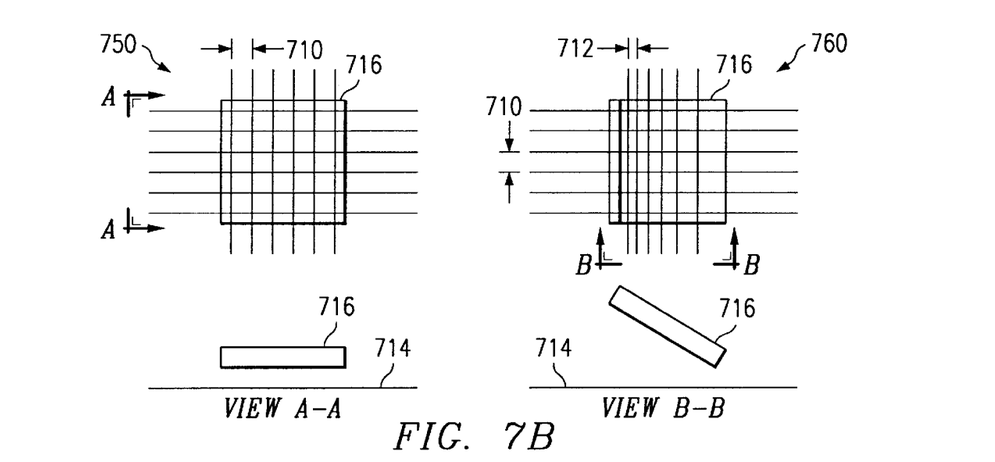

FIGS. 7A and 7B are diagrams 700, 750 and 760 showing illumination of a device or component in accordance with exemplary embodiments of the present invention. Diagrams 700, 750, and 760 demonstrate exemplary features that may be analyzed to determine the plane relative to a normal plane in which a device or component lies.

Diagram 700 includes device 716 having lead 718. A laser light source at location "A" traces a grid pattern on device 716 and lead 718. As shown, this grid pattern creates light areas 702 and 706, and dark areas 704 and 708. Thus, an imaging system having an aperture at point "A" would perceive a continuous line along the length of lead 718, even though the dark areas 704 and 708 are present. Likewise, an imaging system having an aperture at point "B" would perceive a broken line, with portions of dark areas 704 and 708 showing. The angular difference between angle "A," which defines a 90 degree angle between point "A" and the plane in which device 716 lies, and angle "B," which defines a 90 degree angle between point "B" and the plane of device 716, may be determined from the length of the dark areas 704 and 708 that are observed at point B. A similar principle may be used to determine the degree between a plane normal to an imaging system and the plane in which device 716 lies.

Diagrams 750 and 760 demonstrate another suitable manner to determine such angular difference between the normal plane of viewing and the plane in which a device or component lies. The plane of device 716 in diagram 750 is parallel to the normal viewing plane 714, and the grid lines in diagram 750 are evenly spaced along leads of device 716, having a spacing 710. The plane of device 716 in diagram 760 is at an angle to the normal viewing plane 714, and the grid lines 712 in diagram 760 have a spacing that is different from the spacing 710 of grid lines along an axis of the device 716 that is not angularly disposed from the normal plane. Thus, it is possible to determine the angle of the plane of device 716 from the normal plane 714 in diagram 760 based upon the difference between spacing 710 and spacing 712.

In operation, geometric principles are used to analyze a grid that is generated and projected on a device 716, in order to determine the angle at which the plane of the device 716 varies from a normal plane to a vantage point. The angular displacement of the plane of the device 716 may then be used to analyze image data of the device to determine whether features of the device have been damaged.

Although preferred and exemplary embodiments of a system and method for generating a grid have been described in detail herein, those skilled in the art will also recognize that various substitutions and modifications may be made to the systems and methods without departing from the scope and spirit of the appended claims.

What is claimed is:

1. A system for inspecting a component comprising:
an imaging system operable to generate digital image data of the component;
a controller coupled to the imaging system, the controller operable to receive the digital image data and to process the digital image data to generate control commands; and
a variable grid generation system coupled to the controller, the variable grid generation system operable to receive the control commands and to generate a grid in response to the control commands; the variable grid generation system further comprising:
a first and second laser, each generating a laser beam having a frequency and wavelength that is different from the light of the other laser;
a first mirror system receiving the first laser beam and moving the laser beam in an "X" axis;
a second mirror system receiving the laser beam and moving the laser beam in a "Y" axis; and
wherein the first mirror system and the second mirror system are controlled by the controller in a coordinated manner so as to generate the grid.

2. The system of claim 1 wherein the imaging system further comprises:
a first camera operable to generate first digital image data of the component;
a second camera operable to generate second digital image data of the component; and
wherein the controller is operable to process the first digital image data and the second digital image data to form complete digital image data of the component.

3. The system of claim 1 wherein the variable grid generation system comprises a laser system operable to generate the grid by repeatedly moving a laser beam in a grid pattern.

4. The system of claim 1 wherein the variable grid generation system further comprises:
a laser operable to generate a laser beam;
a mirror system operable to receive the laser beam and to move the laser beam so as to form the grid.

5. The system of claim 1 wherein the first mirror system further comprises a first galvanometer coupled to a first mirror, the first galvanometer operable to controllably rotate the first mirror at a variable speed, and a second galvanometer coupled to a second mirror, the second galvanometer operable to controllably rotate the second mirror at a variable speed.

6. The system of claim 1 wherein the controller further comprises an image analyzer system, the image analyzer operable to determine from the image data whether the grid is aligned with one or more predetermined features of the component, and to generate control commands to cause the grid to change so as to be aligned with the predetermined features.

7. The system of claim 1 wherein the controller further comprises a location system, the location system operable to determine the angle at which a plane extending through the component differs from a reference plane from the image data.

8. The system of claim 1 wherein the controller further comprises a laser control system, the laser control system operable to generate laser beam-movement commands based upon the image data.

* * * * *